United States Patent [19]
Holm et al.

[11] 3,970,443
[45] July 20, 1976

[54] CYCLOHEXIMIDE-CYANOBENZENE COMPOSITIONS AS FRUIT ABSCISSION

[75] Inventors: Robert E. Holm, Painesville; Paul H. Schuldt, Mentor, both of Ohio

[73] Assignee: Diamond Shamrock Corporation, Cleveland, Ohio

[22] Filed: Feb. 18, 1975

[21] Appl. No.: 550,525

[52] U.S. Cl.................................. 71/94; 71/105; 71/74; 71/70
[51] Int. Cl.² ........................................ A01N 9/22
[58] Field of Search .................. 71/94, 105, 74, 70

[56] References Cited
UNITED STATES PATENTS

| | | | |
|---|---|---|---|
| 3,290,353 | 12/1966 | Baltershell et al. | 71/105 X |
| 3,663,199 | 5/1972 | Cooper | 71/94 |

Primary Examiner—Lewis Gotts
Assistant Examiner—Catherine L. Mills
Attorney, Agent, or Firm—Timothy E. Tinkler

[57] ABSTRACT

A combination of cycloheximide and chlorinated di- and tricyanobenzenes is a synergistic composition capable of promoting fruit, especially citrus fruit, abscission when applied to trees bearing same.

3 Claims, No Drawings

CYCLOHEXIMIDE-CYANOBENZENE COMPOSITIONS AS FRUIT ABSCISSION

BACKGROUND OF THE INVENTION

The desirability of facilitating the harvest of various agricultural crops, especially fruit crops such as citrus fruits, is readily apparent. A number of chemical compounds capable of promoting fruit abscission has been proposed, which compounds serve to reduce the pull force necessary to remove mature fruit from the tree or plant. Few of these compounds, however, have found practical utility, mainly owing to their tendency to injure immature fruit and cause blossom drop, therefore lessening overall production, and/or their simultaneous defoliant effect.

One compound currently in use as a citrus fruit abscission agent is cycloheximide, i.e., 3(2-[3,5-dimethyl-2-oxocyclohexyl]-2-hydroxyethyl) glutarimide. This use is described more fully in U.S. Pat. 3,663,199. While the compound is indeed effective in reducing the pull force necessary to remove citrus fruit from trees, its use has been seasonally limited on some citrus varieties (e.g. Valencia oranges) since its application in an amount sufficient to cause the desired abscission, can also result in damage to immature fruit and cause leaf and bloom drop.

STATEMENT OF THE INVENTION

Therefore, it is an object of the present invention to provide a method capable of promoting seasonwide abscission of mature fruit, while reducing undesirable side effects.

It is a further object of the present invention to increase the ability of cycloheximide to promote fruit abscission.

These and other objects of the present invention will become apparent to those skilled in the art from the specification and claims that follow.

A method of harvesting mature fruit from a tree has now been found which comprises applying to the fruit locus an abscission-promoting amount of a composition consisting essentially of cycloheximide and a cyanobenzene having the formula:

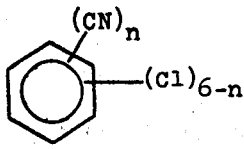

wherein $n$ is 2 or 3, and subsequently exerting a sufficient force on said fruit to remove same. Preferred is a combination of cycloheximide and tetrachloroisophthalonitrile (tetrachloro-1,3-dicyanobenzene).

DESCRIPTION OF THE PREFERRED EMBODIMENTS

Throughout the specification and claims, the term "fruit" is used to define a variety of agricultural products, the removal of which from the parent plant or tree (hereinafter, tree) may be promoted by the use of an abscission agent. Typically included are oranges, lemons, grapefruit, limes, olives, cherries, apples, pecans, and walnuts. Especially important, and referred to particularly hereinafter, are the citrus fruits.

It has been theorized and substantially demonstrated that one abscission mechanism involves the increased production of ethylene within the fruit, which triggers the abscission process. Cycloheximide in one such compound which, when applied externally to mature fruit, increases internal ethylene production and, shortly thereafter, reduces the pull force necessary to remove the fruit. We have confirmed a direct correlation between the ability of a compound or composition to stimulate internal fruit ethylene production and its ability to facilitate fruit abscission.

The present invention makes use of the ability of certain cyanobenzenes to increase this internal ethylene production, i.e., the amount of ethylene produced per a given quantity of cycloheximide is significantly increased. A reduction in the pull force necessary to cause abscission follows. This is thought to be surprising since the cyanobenzenes themselves do not act to produce any significant quantities of ethylene in fruit when externally applied. Thus, the invention allows the use of a lesser quantity of cycloheximide, thereby reducing injury to the tree and any blooms and immature fruit, or causes an increased abscission-promoting effect at the same cycloheximide concentration. While higher amounts have been recommended when applying cycloheximide alone, the present invention demonstrates commercially acceptable results at cycloheximide concentrations in the applied formulation within the range of from 2 to 20 especially 5–15, parts per million.

As stated above, the cyanobenzenes effective in combination with cycloheximide according to the present invention have the formula:

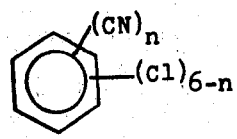

wherein $n$ is 2 or 3, that is, the positional tetrachlorodicyanobenzene and trichlorotricyanobenzene isomers. Typical are tetrachloroisophthalonitrile and 2,4,6-trichlorotricyanobenzene. Particularly preferred at this time is tetrachloroisophthalonitrile. The cyanobenzenes may be employed alone or in combination and at a total concentration ranging between 25 and 1000 ppm. The ratio of cyanobenzene to cycloheximide is within the range of from 10–100:1, preferably 10–50:1, by weight.

The composition will generally be applied as an aqueous spray, this being most convenient and economical, although dusting or other methods of application are possible. Preparation of the aqueous formulation merely requires the dispersion or emulsification of the generally water-insoluble cyanobenzene materials at the stated concentration ranges employing a non-phytotoxic surfactant, such as polyoxyethylated sorbitan monolaurate.

Thus, when the fruit has reached substantial maturity, the abscission promoting composition is applied, generally 5 to 10 days prior to the desired harvesting date, by spraying the fruit locus, although the entire tree may be treated for convenience. Application may be by low volume spray, to run-off, or otherwise as may be desired. Harvesting is then accomplished by exerting sufficient force on the fruit to remove it from the tree.

Often, the weight of the fruit alone will cause it to fall from the tree, demonstrating a pull force of less than 0.5 kg. More typically, some positive force must be applied, such as mechanical shaking or from air or water guns.

In order that those skilled in the art may more readily understand the present invention and certain preferred embodiments by which it may be carried into effect, the following specific examples are afforded.

EXAMPLE I

The ability of the present invention to increase internal ethylene production on external application to fruit is demonstrated by this Example. Tetrachloroisophthalonitrile (TCIPN) is provided as a 40% by weight formulation in aqueous suspension with a nonionic surfactant and thickening, anticaking, anti-foaming, and freeze-point depressing agents. Aqueous solutions of cycloheximide (CHI) and/or TCIPN are prepared in concentrations such that 1 ml. contains the amount of active ingredient(s) set forth in the following Table I. Valencia oranges were then purchased and selected for uniformity of size, color, and shape and freedom from imperfections. These oranges were then sprayed with 1 ml. of the solution in question, loosely covered with clear plastic, and placed in a growth chamber maintained at 24°C daytime and 16°C nighttime with a light intensity of 800 $\mu$ E/m$^2$/sec. At the indicated intervals a syringe was employed to extract a gas sample from inside the orange near the stem area, which sample was then analyzed for ethylene by gas chromatography on an instrument sensitive to the 10 ppb level. The asterisk (*) in this and following tables indicates a control sample in which there was applied to the orange an aqueous spray of the formulation base mentioned above (i.e., nonionic surfactant, thickening agent, etc. but no TCIPN). Each result reported is the average of four replicated tests.

Table I

| CHI ($\mu$g/fruit) | TCIPN ($\mu$g/fruit) | Internal Ethylene (ppm/ml) | |
|---|---|---|---|
| | | 3 day | 7 day |
| 0 | 0 | 0.07 | 0.09 |
| 0 | 0* | 0.07 | 0.09 |
| 5 | 0 | 1.24 | 0.36 |
| 0 | 50 | 0.12 | 0.15 |
| 0 | 100 | 0.15 | 0.13 |
| 0 | 250 | 0.12 | 0.07 |
| 0 | 500 | 0.18 | 0.15 |

Table I-continued

| CHI ($\mu$g/fruit) | TCIPN ($\mu$g/fruit) | Internal Ethylene (ppm/ml) | |
|---|---|---|---|
| | | 3 day | 7 day |
| 5 | 50 | 1.67 | 1.04 |
| 5 | 100 | 2.11 | 0.68 |
| 5 | 250 | 2.13 | 0.73 |
| 5 | 500 | 1.22 | 0.41 |

From Table I the increase in internal ethylene production is readily apparent upon the addition of TCIPN. This occurs even though neither the TCIPN nor the formulation base has any significant effect on ethylene production. Significantly, the ethylene values remain at elevated levels for longer periods of time when the combination of ingredients is employed. This allows more latitude in harvesting the fruit in the event, for example, of climatic interruptions.

EXAMPLE II

To demonstrate the utility of the present invention on Valencia oranges, as opposed to the use of cycloheximide alone, the following tests were conducted during a growing season. In each instance a branch on a Valencia orange tree, bearing from 20 to 30 mature fruit, was treated to run-off with aqueous solutions as indicated in Table II. The TCIPN was again provided in the formulation as described in Example I. Seven days after spray application of the abscission agents the observations appearing in Table II were recorded.

Table II

| Time of Application | CHI (ppm) | TCIPN (ppm) | Pull Force (kg) | Mature Fruit Damage (1) | Bloom Drop (%) | Defoliation (%) | Green Fruit Drop (%) |
|---|---|---|---|---|---|---|---|
| Mid-April | 0 | 0 | 9.25 | 0 | 0 | 0 | 0 |
| " | 20 | 0 | 0.45 | H | 100 | 25 | 98 |
| " | 7.5 | 250 | 0.45 | M/H | 0 | 0 | 0 |
| Mid-May | 0 | 0 | 8.80 | 0 | — (2) | 0 | 0 |
| " | 20 | 0 | 0.45 | M/L | — | 8 | 5 |
| " | 7 | 50 | 0.45 | M | — | 8 | 5 |
| Mid-June | 0 | 0 | 10.3 | 0 | — | 0 | 0 |
| " | 20 | 0 | 3.58 | M | — | 8 | 5 |
| " | 15 | 50 | 1.77 | H | — | 4 | 0 |

(1) L=light
M=moderate
H=heavy (2) no bloom present

The first application shows the ability of the abscission composition of the present invention to maintain a good reduction in pull force while eliminating harmful side effects obtained with CHI alone, such as green fruit and bloom drop. In later applications, where immature fruits or bloom were not present, results were as good or better than with cycloheximide alone.

EXAMPLE III

In this Example the comparative effect of the present invention is evaluated on growing Hamlin oranges. Each test reported in Table III is the average of two treatments of approximately 20 to 30 oranges per treatment. Application was by spraying until run-off of the fruit and surrounding portions of the trees. Again, application of the TCIPN was from the formulated material described in Example I. The units for both CHI and TCIPN in Table III are parts per million.

Table III

| CHI | TCIPN | Pull Force (kg) | CHI | TCIPN | Pull Force(kg) | CHI | TCIPN | Pull Force(kg) | Mature Fruit Fall(%) |
|---|---|---|---|---|---|---|---|---|---|
| 0 | 0 | 7.26 | 0 | 0 | 7.26 | 0 | 0 | 7.26 | 0 |
| 0 | 0* | 7.26 | 0 | 0* | 7.26 | 0 | 0* | 7.26 | 0 |
| 20 | 0 | 2.19 | 20 | 0 | 2.19 | 20 | 0 | 2.19 | 0 |
| 5 | 0* | 4.44 | 10 | 0* | 3.29 | 15 | 0* | 2.30 | 0 |
| 5 | 50 | 3.53 | 10 | 50 | 2.93 | 15 | 50 | 2.39 | 50 |
| 5 | 100 | 3.43 | 10 | 100 | 2.76 | 15 | 100 | 2.20 | 25 |
| 5 | 200 | 3.39 | 10 | 200 | 2.20 | 15 | 200 | 1.81 | 22 |
| 5 | 300 | 2.95 | 10 | 300 | 2.46 | 15 | 300 | 1.84 | 17 |
| 5 | 400 | 3.16 | 10 | 400 | 1.94 | 15 | 400 | 1.36 | 7 |
| 5 | 500 | 2.76 | 10 | 500 | 2.39 | 15 | 500 | 1.47 | 20 |

Table III demonstrates the reduction in pull force that is obtainable using lower amounts of cycloheximide when employed in combination with TCIPN. With respect to the last section of the table, where mature fruit fall is also measured, it should be pointed out that this represents the amount of fruit that has fallen of its own weight from the tree, thus evidencing a pull force of less than 0.5 kg. These values are not included in the reported pull force for the fruit remaining on the tree. Obviously, the average pull force would be much lower if the fallen fruit values were included.

We claim:

1. A method of harvesting mature fruit from a tree, which method comprises applying to the fruit locus an abscission-promoting amount of a composition consisting essentially of cycloheximide and tetrachloroisophthalonitrile and subsequently exerting a sufficient force on said fruit to remove same.

2. A method as in claim 1 wherein said amount is applied by run-off of a formulation containing from 2 to 20 ppm cycloheximide and from 25 to 1000 ppm of tetrachloroisophthalonitrile.

3. A method as in claim 1 wherein from 10 to 50 parts of tetrachloroisophthalonitrile is present per part of cycloheximide.

* * * * *